(12) United States Patent
Park et al.

(10) Patent No.: US 8,658,805 B2
(45) Date of Patent: Feb. 25, 2014

(54) FUSED POLYHETEROAROMATIC COMPOUND, ORGANIC THIN FILM INCLUDING THE COMPOUND, AND ELECTRONIC DEVICE INCLUDING THE ORGANIC THIN FILM

(71) Applicant: Samsung Electronics, Co., Ltd., Suwon-Si (KR)

(72) Inventors: Jeong Il Park, Seongnam-si (KR); Bang Lin Lee, Suwon-si (KR); Ji Youl Lee, Seoul (KR); Jong Won Chung, Hwaseong-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/670,196

(22) Filed: Nov. 6, 2012

(65) Prior Publication Data

US 2013/0116447 A1 May 9, 2013

(30) Foreign Application Priority Data

Nov. 7, 2011 (KR) ........................ 10-2011-0115235

(51) Int. Cl.
*C07D 495/22* (2006.01)

(52) U.S. Cl.
USPC .......................................................... 549/41

(58) Field of Classification Search
USPC .................................................... 549/24, 41
See application file for complete search history.

(56) References Cited

U.S. PATENT DOCUMENTS

| | | | |
|---|---|---|---|
| 5,198,153 | A | 3/1993 | Angelopoulos et al. |
| 5,892,244 | A | 4/1999 | Tanaka et al. |
| 5,946,551 | A | 8/1999 | Dimitrakopoulos et al. |
| 5,981,970 | A | 11/1999 | Dimitrakopoulos et al. |
| 5,998,804 | A | 12/1999 | Suh et al. |
| 6,210,479 | B1 | 4/2001 | Bojarczuk et al. |
| 6,215,130 | B1 | 4/2001 | Dodabalapur |
| 6,232,157 | B1 | 5/2001 | Dodabalapur et al. |
| 6,344,660 | B1 | 2/2002 | Dimitrakopoulos et al. |
| 6,344,662 | B1 | 2/2002 | Dimitrakopoulos et al. |
| 6,913,710 | B2 | 7/2005 | Farrand et al. |
| 7,816,673 | B2 | 10/2010 | Park et al. |
| 8,232,546 | B2 | 7/2012 | Takimiya et al. |
| 2008/0142792 | A1 | 6/2008 | Park et al. |
| 2010/0065826 | A1 | 3/2010 | Takimiya et al. |
| 2011/0303910 | A1 | 12/2011 | Kuwabara et al. |
| 2012/0193618 | A1 | 8/2012 | Takeya et al. |

FOREIGN PATENT DOCUMENTS

| | | | | |
|---|---|---|---|---|
| JP | 2009099658 A | * | 5/2009 | .............. H01L 51/30 |
| JP | 2009-218335 A | | 9/2009 | |
| JP | 2010-177643 A | | 8/2010 | |
| KR | 10-2008-0054553 A | | 6/2008 | |
| WO | WO-2008/050726 A1 | | 5/2008 | |
| WO | WO-2009/009790 A1 | | 1/2009 | |
| WO | WO-2010/098372 A1 | | 9/2010 | |
| WO | WO-2011/040155 A1 | | 4/2011 | |

OTHER PUBLICATIONS

Yamamoto et al., Largely pi-Extended Thienoacenes with Internal Thieno[3,2-b]thiophene Substructures: Synthesis, Characterization, and Organic Field-Effect Transistor Applications, 2012, Org. Lett., vol. 14, No. 18, 4914-4917.*
Kengo Nakayama, et al. Adv. Mater. 2011, 23(14), "Patternable Solution-Crystallized Organic Transistors with High Charge Carrier Mobility", 1626-1629.
Hiromi Minemawari, et al. Nature, 2011, "Inkjet printing of single-crystal films".
Kazuki Niimi, et al. J. Am. Chem. Soc. 2011, 133 (22), "Dianthra[2,3-b:2',3'-f]thiophene (DATT): Synthesis, Characterization, and FET Characteristics of New π-Extended Heteroarene with Eight Fused Aromatic Rings", 8732-8739.
Anatoliy N. Sokolov, et al. Nature Communications. "From computational discovery to experimental characterization of a high hole mobility organic crystal", 2011.
Wex, et al., "Synthesis of the *anti* and *syn* isomers of thieno[f,f']bis[1]benzothiophene. Comparison of the optical and electrochemical properties of the *anti* and *syn* isomers", J. Org. Chemistry, 2005, 70, pp. 4502-4505.

* cited by examiner

*Primary Examiner* — Kristin Vajda
(74) *Attorney, Agent, or Firm* — Harness, Dickey & Pierce, P.L.C.

(57) ABSTRACT

A low-molecular-weight fused polycyclic heteroaromatic compound may have a compact planar structure in which seven or more rings are fused together. The compound may exhibit a relatively high charge mobility and enable the use of a deposition process or a room-temperature solution process when applied to devices, therefore realizing improved processibility. An organic thin film and electronic device may include the fused polycyclic heteroaromatic compound.

12 Claims, 2 Drawing Sheets

FUSED POLYHETEROAROMATIC COMPOUND, ORGANIC THIN FILM INCLUDING THE COMPOUND, AND ELECTRONIC DEVICE INCLUDING THE ORGANIC THIN FILM

CROSS-REFERENCE TO RELATED APPLICATION

This application claims priority under 37 U.S.C. §119 to Korean Patent Application No. 10-2011-0115235, filed in the Korean Intellectual Property Office (KIPO) on Nov. 7, 2011, the entire contents of which are incorporated herein by reference.

BACKGROUND

1. Field

Example embodiments relate to a fused polycyclic heteroaromatic compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, as a material for a channel of the TFT, organic materials, e.g., pentacene or polythiophene, have been studied. In the case of polymer or oligomer organic materials, e.g., F8T2 (poly(9,9-dioctylfluorene-co-bithiophene)) as a polythiophene-based material, a solution process, e.g., spin casting, may be desirably applied. However, problems of decreased charge mobility and increased off-state leakage current may occur. Further, low-molecular-weight organic materials, e.g., pentacene, may have a relatively high charge mobility of about 3.2 to about 5.0 cm$^2$/Vs or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

Thus, there have been attempts to devise materials for channel layers having increased charge mobility and improved processibility. The related art discloses dimeric bisbenzodithiophene, in which rings may be fused in groups of three and thus increased charge mobility may be realized.

However, the development of an organic semiconductor material, satisfying improved electrical properties and processibility, may still be required in the art.

SUMMARY

Various example embodiments relate to a low-molecular-weight fused polycyclic heteroaromatic compound that has a compact planar structure in which seven or more rings are fused together, and thereby exhibits high charge mobility, and furthermore, enables the use of a deposition process or a room-temperature solution process when applied to devices, therefore realizing improved processibility.

Various example embodiments relate to an organic thin film including the fused polycyclic heteroaromatic compound.

Various example embodiments relate to an electronic device including the organic thin film as a carrier transport layer.

A fused polycyclic heteroaromatic compound may be selected from a compound represented by the following Chemical Formula 1A, a compound represented by the following Chemical Formula 1B, and a combination thereof.

[Chemical Formula 1A]

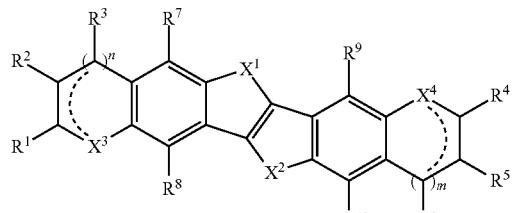

[Chemical Formula 1B]

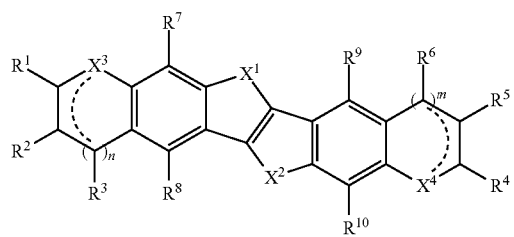

In Chemical Formulas 1A and 1B, $X^1$ and $X^2$ are each independently O, S, Se, Te, or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroaryl group, an acyl group (—C(═O)$R^{13}$, wherein $R^{13}$ is a substituted or unsubstituted C1 to C30 alkyl group), a sulfonyl group (—S(═O)$R^{14}$, wherein $R^{14}$ is a substituted or unsubstituted C1 to C30 alkyl group), or a carbamate group (—$NH_2COOR^{15}$, wherein $R^{15}$ is a substituted or unsubstituted C1 to C30 alkyl group), $X^3$ and $X^4$ are each independently O, S, Se, Te, N, N—$R^a$, or C$R^b$, wherein $R^a$ and $R^b$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroaryl group, an acyl group (—C(═O)$R^{13}$, wherein $R^{13}$ is a substituted or unsubstituted C1 to C30 alkyl group), a sulfonyl group (—S(═O)$R^{14}$, wherein $R^{14}$ is a substituted or unsubstituted C1 to C30 alkyl group), or a carbamate group (—$NH_2COOR^{15}$, wherein $R^{15}$ is a substituted or unsubstituted C1 to C30 alkyl group), provided that both $X^3$ and $X^4$ are not $CR^b$, $R^1$, $R^2$, $R^3$, $R^4$, $R^5$, $R^6$, $R^7$, $R^8$, $R^9$, and $R^{10}$ are each independently hydrogen, a halogen (—F, —Cl, —Br, or —I), a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, provided that at least one pair of substituents selected from $R^1$ and $R^2$, and $R^2$ and $R^3$, are linked to provide an aromatic ring, a heteroaromatic ring, or an alicyclic ring fused with a $X^3$-containing ring, or at least one pair of substituents selected from $R^4$ and $R^5$, and $R^5$ and $R^6$, are linked to provide an aromatic ring, a heteroaromatic ring, or an alicyclic ring fused with a $X^4$-containing ring, and n and m are integers of 0 or 1, and are not simultaneously 1.

$R^1$, $R^2$, $R^3$, $R^4$, $R^5$, or $R^6$ that does not provide a fused ring in the $X^3$-containing ring or $X^4$-containing ring may be a substituted or unsubstituted C10 to C30 alkyl group or a substituted or unsubstituted C10 to C30 alkenyl group. At least one selected from $R^7$, $R^8$, $R^9$, and $R^{19}$ is a substituted or unsubstituted C10 to C30 alkyl group or a substituted or unsubstituted C10 to C30 alkenyl group.

The fused polycyclic heteroaromatic compound may be a fused polycyclic heteroaromatic compound represented by the following Chemical Formula 2A or 2B.

[Chemical Formula 2A]

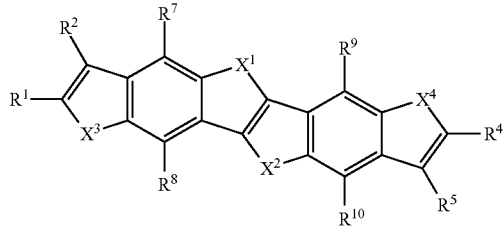

[Chemical Formula 2B]

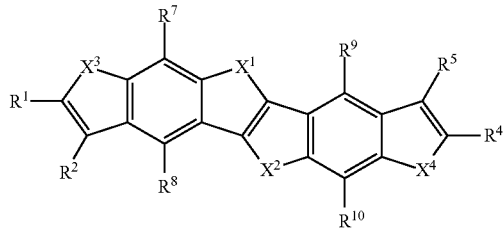

In Chemical Formulas 2A and 2B,
$X^1$, $X^2$, $X^3$, $X^4$, $R^1$, $R^2$, $R^4$, $R^5$, $R^7$, $R^8$, $R^9$, and $R^{10}$ are the same as in Chemical Formulas 1A and 1B, provided that $R^1$ and $R^2$ are linked to each other to provide an aromatic ring, a heteroaromatic ring, or an alicyclic ring fused with an $X^3$-containing ring, or $R^4$ and $R^5$ are linked to each other to provide an aromatic ring, a heteroaromatic ring, or an alicyclic ring fused with a $X^4$-containing ring.

In Chemical Formulas 2A and 2B, $X^1$, $X^2$, $X^3$, and $X^4$ may be sulfur (S).

The fused polycyclic heteroaromatic compound may be a fused polycyclic heteroaromatic compound represented by the following Chemical Formula 3A or 3B.

[Chemical Formula 3A]

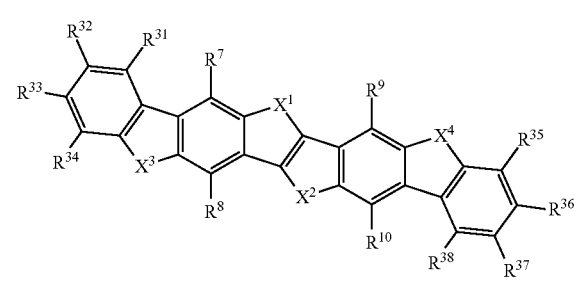

[Chemical Formula 3B]

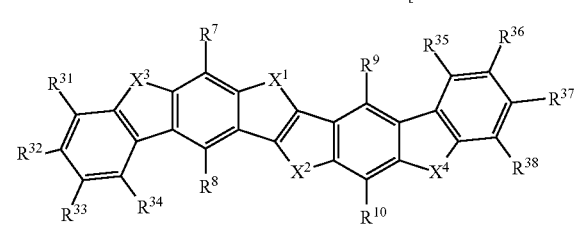

In Chemical Formulas 3A and 3B, $X^1$, $X^2$, $X^3$, $X^4$, $R^7$, $R^8$, $R^9$, and $R^{10}$ are the same as in Chemical Formulas 1A and 1B, $R^{31}$ to $R^{38}$ are each independently hydrogen, a halogen (—F, —Cl, —Br or —I), a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, or two selected from $R^{31}$ to $R^{34}$ or two selected from $R^{35}$ to $R^{38}$ may be linked to the adjacent functional group to provide an aromatic ring, a heteroaromatic ring, or an alicyclic ring fused with the $C_6$-aryl ring.

In Chemical Formulas 3A and 3B, $X^1$, $X^2$, $X^3$, and $X^4$ may be sulfur (S).

The fused polycyclic heteroaromatic compound may be a fused polycyclic heteroaromatic compound represented by the following Chemical Formula 4A or 4B.

[Chemical Formula 4A]

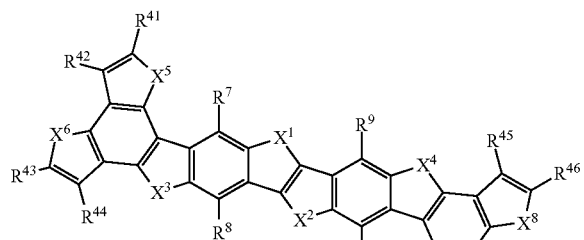

[Chemical Formula 4B]

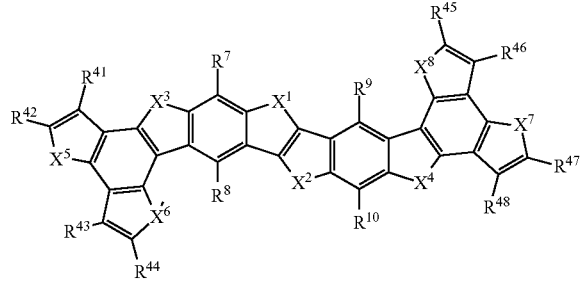

In Chemical Formulas 4A and 4B, $X^1$, $X^2$, $X^3$, $X^4$, $R^7$, $R^8$, $R^9$, and $R^{10}$ are the same as in Chemical Formulas 1A and 1B, $X^5$ to $X^8$ are each independently O, S, Se, Te, N—$R^a$, or $CR^bR^c$, wherein $R^a$ to $R^c$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroarylalkyl group, a substituted or unsubstituted C2 to C30 alkylheteroaryl group, an acyl group (—C(=O)$R^{13}$, wherein $R^{13}$ is a substituted or unsubstituted C1 to C30 alkyl group), a sulfonyl group (—S(=O)$R^{14}$, wherein $R^{14}$ is a substituted or unsubstituted C1 to C30 alkyl group), or a carbamate group (—$NH_2COOR^{15}$, wherein $R^{15}$ is a substituted or unsubstituted C1 to C30 alkyl group), and $R^{41}$ to $R^{48}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, or at least one pair of substituents selected from $R^{41}$ and $R^{42}$, $R^{43}$ and $R^{44}$, $R^{45}$ and $R^{46}$, and $R^{45}$ and $R^{46}$ may be linked to each other to provide an aromatic ring, a heteroaromatic ring, or an alicyclic ring fused with at least one of a $X^5$-containing ring, a $X^6$-containing ring, a $X^7$-containing ring, and $X^8$-containing ring.

In Chemical Formulas 4A and 4B, $X^1$, $X^2$, $X^3$, $X^4$, $X^5$, $X^6$, $X^7$, and $X^8$ may be sulfur (S).

The fused polycyclic heteroaromatic compound may be a fused polycyclic heteroaromatic compound represented by the following Chemical Formula 5A or 5B.

[Chemical Formula 5A]

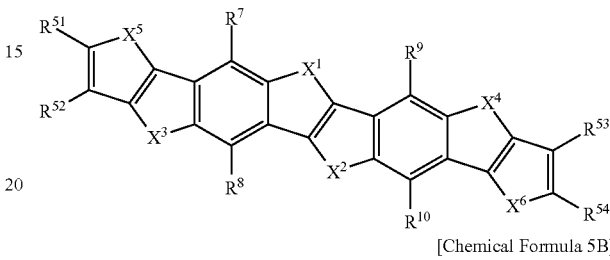

[Chemical Formula 5B]

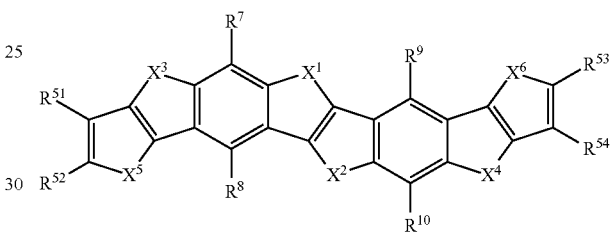

In Chemical Formulas 5A and 5B, $X^1$, $X^2$, $X^3$, $X^4$, $R^7$, $R^8$, $R^9$, and $R^{10}$ are the same as in Chemical Formulas 1A and 1B, $X^5$ and $X^6$ are each independently O, S, Se, Te, N—$R^a$, or $CR^bR^c$, wherein $R^a$ to $R^c$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroaryl group, an acyl group (—C(=O)$R^{13}$, wherein $R^{13}$ is a substituted or unsubstituted C1 to C30 alkyl group), a sulfonyl group (—S(=O)$R^{14}$, wherein $R^{14}$ is a substituted or unsubstituted C1 to C30 alkyl group), or a carbamate group (—$NH_2COOR^{15}$, wherein $R^{15}$ is a substituted or unsubstituted C1 to C30 alkyl group), and $R^{51}$ to $R^{54}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, or at least one pair of substituents selected from $R^{51}$ and $R^{52}$, and $R^{53}$ and $R^{54}$, may be linked to each other to provide an aromatic ring, a heteroaromatic ring, or an alicyclic ring fused with a $X^5$-containing ring or fused with a $X^6$-containing ring.

In Chemical Formula 5A or 5B, $X^1$, $X^2$, $X^3$, $X^4$, $X^5$, and $X^6$ may be sulfur (S).

The fused polycyclic heteroaromatic compound may have an average molecular weight of about 350 to about 3000.

An organic thin film and/or an electronic device may include the fused polycyclic heteroaromatic compound.

Figure 1:
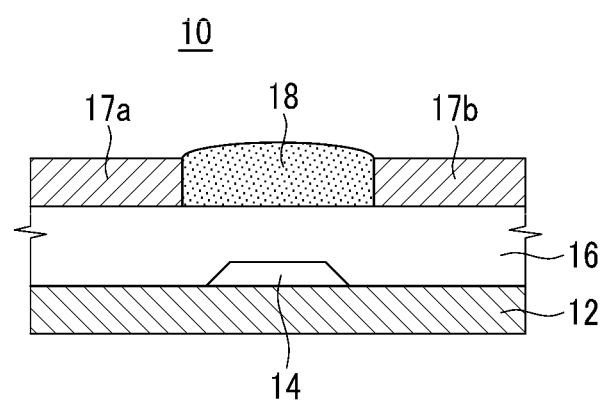
FIG. 1 is a schematic cross-sectional view of a transistor according to example embodiments.

It should be noted that the provided figures are merely intended to illustrate the general characteristics of the methods, structures, and/or materials utilized in various example embodiments and to supplement the written description provided below. However, the drawings may not have been drawn, to scale and may not reflect the precise structural or performance characteristics of any given embodiment and should not be interpreted as defining or limiting the range of values or properties encompassed by example embodiments. For example, the relative thicknesses and/or positioning of the molecules, layers, regions and/or structural elements may have been reduced or exaggerated for clarity. The use of similar or identical reference numbers in the various drawings is intended to indicate the presence of a similar or identical element or feature.

DETAILED DESCRIPTION

Example embodiments will now be described more fully with reference to the accompanying drawings. However, it should be understood that the examples may be embodied in many different forms and should not be construed as being limited to the embodiments set forth herein. Rather, these embodiments are merely provided so that this disclosure will be more thorough and complete and will assist in fully conveying the concept of example embodiments to those of ordinary skill in the art. In the drawings, the thicknesses of layers and regions may have been exaggerated for clarity. Like reference numerals in the drawings denote like elements, and thus their description in a similar drawing may be omitted for purposes of brevity.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments are described herein with reference to cross-sectional illustrations that are schematic illustrations of idealized embodiments (and perhaps intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

As used herein, the term "combination thereof" refers to a mixture, a stacked structure, a composite, an alloy, or the like.

As used herein, when a definition is not otherwise provided, the term "hetero" may refer to one including 1 to 4 heteroatoms selected from N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an isoamyl group, a hexyl group, and the like).

The term "alkenyl group" may refer to a linear or branched saturated monovalent hydrocarbon group including at least one carbon-carbon double bond (e.g., an ethenyl group).

The term "alkynyl group" may refer to a linear or branched saturated monovalent hydrocarbon group including at least one carbon-carbon triple bond (e.g., an ethynyl group).

The term "alkoxy group" may refer to an alkyl group that is linked via an oxygen, e.g., a methoxy, an ethoxy, and a sec-butyloxy group.

The term "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons wherein the additional ring(s) of the polycyclic hydrocarbon may be aromatic or nonaromatic.

The term "aryloxy group" may refer to an aryl group that is linked via an oxygen, and the aryl group is the same as described above.

The "arylalkyl group" may refer to an aryl group where at least one hydrogen is substituted with a lower alkylene, e.g., methylene, ethylene, propylene, and the like. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "cycloalkenyl group" may refer to a monovalent functional group including at least one ring having a carbon-carbon double bond, wherein all ring members are carbon, e.g., a cyclopentenyl group or a cyclohexenyl group.

The term "heteroarylalkyl group" may refer to an alkyl group where at least one hydrogen is substituted with a heteroaryl group.

The term "alkylheteroaryl group" may refer to a heteroaryl group where at least one hydrogen is substituted with an alkyl group.

As used herein, when a definition is not otherwise provided, "aromatic ring" refers to a functional group in which all atoms in the cyclic functional group have a p-orbital, wherein these p-orbitals are conjugated. For example, the aromatic ring may be a C6 to C20 aryl group.

As used herein, when a definition is not otherwise provided, "heteroaromatic ring" refers to a functional group including a heteroatom selected from N, O, and S in a ring in which all atoms in the cyclic functional group have a p-orbital, wherein the p-orbital is conjugated. For example, the heteroaromatic ring may be a C2 to C20 heteroaryl group.

As used herein, when a definition is not otherwise provided, the term "alicyclic ring" may refer to non-conjugated ring, for example a C3 to C20 cycloalkyl group, a C3 to C20 heterocycloalkyl group, a C3 to C20 cycloalkenyl group, a C3 to C20 heterocycloalkenyl group, and the like.

As used herein, when a definition is not otherwise provided, the term "substituted" means that the compound or group is substituted with at least one substituent selected independently from a halogen (—F, —Cl, —Br, or —I), a C1 to C30 linear or branched alkyl group, for example a C1 to C10 linear or branched alkyl group, C2 to C30 linear or branched alkenyl group, for example a C2 to C10 linear or branched alkenyl group, a C2 to C30 linear or branched alkynyl group, for example a C2 to C10 linear or branched alkynyl group, a C6 to C30 aryl group, for example a C6 to C12 aryl group, a C2 to C30 heteroaryl group, for example a C2 to C12 heteroaryl group, a C3 to C30 cycloalkyl group, a C1 to C20 fluoroalkyl group, a C1 to C20 perfluoroalkyl group ($C_nF_{2n+1}$), a C1 to C30 linear or branched alkoxy group, a C3 to C30 cycloalkoxy group, a C2 to C30 linear or branched alkoxyalkyl group, a C4 to C30 cycloalkoxyalkyl group, a cyano group, an amino group (—NRR', wherein R and R' are independently hydrogen or a C1 to C10 alkyl group), an amidino group (—C(=NH)NH$_2$), a nitro group (—NO$_2$), an amide group (—C(=O)N(H)R, wherein R is hydrogen or a C1 to C10 alkyl group), an aldehyde group (—C(=O)H), a hydroxyl group (—OH), a sulfonyl group (—S(=O)$_2$R, wherein R is independently hydrogen or a C1 to C10 alkyl group), and a carbamate group (—NH$_2$COOR, wherein R is a C1 to C10 alkyl group) instead of hydrogen, provided that the substituted atom's normal valence is not exceeded.

A fused polycyclic heteroaromatic compound may have a compact planar structure in which seven or more rings may be fused together involving the following Chemical Formula 1A or 1B.

[Chemical Formula 1A]

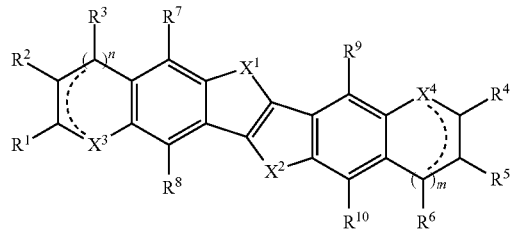

[Chemical Formula 1B]

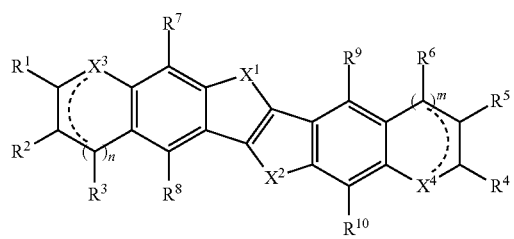

In Chemical Formulas 1A and 1B, $X^1$ and $X^2$ are each independently O, S, Se, Te, or N—$R^a$, wherein $R^a$ is hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example a C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—$C(=O)R^{13}$, wherein $R^{13}$ is a substituted or unsubstituted C1 to C30 alkyl group, for example a C1 to C20 alkyl group), a sulfonyl group (—$S(=O)R^{14}$, wherein $R^{14}$ is a substituted or unsubstituted C1 to C30 alkyl group, for example a C1 to C20 alkyl group), or a carbamate group (—$NH_2COOR^{15}$, wherein $R^{15}$ is a substituted or unsubstituted C1 to C30 alkyl group, for example a C1 to C20 alkyl group), $X^3$ and $X^4$ are each independently O, S, Se, Te, N, N—$R^a$, or $CR^b$, wherein $R^a$ and $R^b$ are each independently hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example a C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—$C(=O)R^{13}$, wherein $R^{13}$ is a substituted or unsubstituted C1 to C30 alkyl group, for example a C1 to C20 alkyl group), a sulfonyl group (—$S(=O)R^{14}$, wherein $R^{14}$ is a substituted or unsubstituted C1 to C30 alkyl group, for example a C1 to C20 alkyl group), or a carbamate group (—$NH_2COOR^{15}$, wherein $R^{15}$ is a substituted or unsubstituted C1 to C30 alkyl group, for example a C1 to C20 alkyl group), provided that both $X^3$ and $X^4$ are not $CR^b$, $R^1$, $R^2$, $R^3$, $R^4$, $R^5$, $R^6$, $R^7$, $R^8$, $R^9$, and $R^{10}$ are each independently hydrogen, a halogen, a substituted or unsubstituted linear or branched C1 to C30 alkyl group, for example a substituted or unsubstituted linear or branched C1 to C20 alkyl group, a substituted or unsubstituted linear or branched C2 to C30 alkenyl group, for example a substituted or unsubstituted linear or branched C2 to C20 alkenyl group, a substituted or unsubstituted linear or branched C2 to C30 alkynyl group, for example a substituted or unsubstituted linear or branched C2 to C20 alkynyl group, a substituted or unsubstituted C7 to C30 arylalkyl group, for example a substituted or unsubstituted C7 to C20 arylalkyl group, a substituted or unsubstituted C2 to C30 heteroarylalkyl group, for example a substituted or unsubstituted C2 to C20 heteroarylalkyl group, a substituted or unsubstituted C2 to C30 alkylheteroaryl group, for example a substituted or unsubstituted C2 to C20 alkylheteroaryl group, a substituted or unsubstituted C5 to C30 cycloalkyl group, for example a substituted or unsubstituted C5 to C20 cycloalkyl group, a substituted or unsubstituted C2 to C30 heterocycloalkyl group, for example a substituted or unsubstituted C2 to C20 heterocycloalkyl group, a substituted or unsubstituted C6 to C30 aryl group, for example a substituted or unsubstituted C6 to C20 aryl group, or a substituted or unsubstituted C2 to C30 heteroaryl group, for example a substituted or unsubstituted C2 to C20 heteroaryl group, provided that at least one pair of substituents selected from $R^1$ and $R^2$, and $R^2$ and $R^3$, are linked to provide an aromatic ring, a heteroaromatic ring, or an alicyclic ring fused with a $X^3$-containing ring, or at least one pair of substituent selected from $R^4$ and $R^5$, and $R^5$ and $R^6$, are linked to provide an aromatic ring, a heteroaromatic ring, or an alicyclic ring fused with a $X^4$-containing ring, and n and m are integers of 0 or 1, and are not simultaneously 1.

The fused polycyclic heteroaromatic compounds represented by the above Chemical Formula 1A or 1B have a structure in which seven or more aromatic rings and heteroaromatic rings are fused. By having a compact planar molecular structure, the compound has a uniform and stable oxidation potential when applied to an actual device and shows high charge mobility since the intermolecular packing and stacking are improved. Thereby, the compound may be synthesized with relative ease so as to be effectively applied to a semiconductor material, an electron transporting material, or the like. In other words, benzene rings are positioned in both Chemical Formulas 1A and 1B in the center of thieno [3,2-b]thiophene, and an $X^3$-containing ring or an $X^4$-containing ring is condensed in the benzene ring to enlarge the conjugation structure and to enhance the intermolecular interaction.

In addition, by positioning a heteroring between benzene rings, the dissolubility of the polycyclic heteroaromatic compound fused to the organic solvent may be improved. By introducing a C10 to C30 long aliphatic chain group (e.g., a substituted or unsubstituted C10 to C30 alkyl group or a substituted or unsubstituted C10 to C30 alkenyl group) into $R^1$, $R^2$, $R^3$, $R^4$, $R^5$, or $R^6$ which does not form an $X^3$-containing ring or an $X^4$-containing ring, or by introducing a C10 to C30 long aliphatic chain group (e.g., a substituted or unsubstituted C10 to C30 alkyl group or a substituted or unsubstituted C10 to C30 alkenyl group) into at least one of $R^7$, $R^8$, $R^9$, and $R^{10}$, the dissolubility of the polycyclic heteroaromatic compound fused to the organic solvent may be improved. Due to the dissolubility improvement, it may be simply coated by a solution process at room temperature as well as in a deposition process, and the thin film may be formed in a wide area so the processibility and the workability are improved.

In Chemical Formula 1A, since $X^1$ and $X^2$, and $X^3$ and $X^4$, are respectively positioned symmetrically to each other, the packing or stacking characteristics may be enhanced.

In the above Chemical Formulas 1A and 1B, $X^1$, $X^2$, $X^3$, and $X^4$ may be sulfur (S).

In Chemical Formula 1A or 1B, when n and m are 0, the fused polycyclic heteroaromatic compound may be represented by the following Chemical Formula 2A or 2B.

[Chemical Formula 2A]

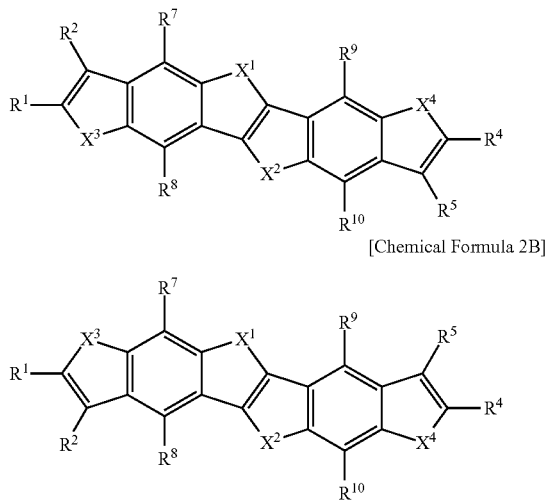

[Chemical Formula 2B]

In Chemical Formulas 2A and 2B, $X^1$, $X^2$, $X^3$, $X^4$, $R^1$, $R^2$, $R^4$, $R^5$, $R^7$, $R^8$, $R^9$, and $R^{10}$ are the same as in Chemical Formulas 1A and 1B, provided that $R^1$ and $R^2$ are linked to each other to provide an aromatic ring, a heteroaromatic ring, or an alicyclic ring fused with an $X^3$-containing ring, or $R^4$ and $R^5$ are linked to each other to provide an aromatic ring, a heteroaromatic ring, or an alicyclic ring fused with an $X^4$-containing ring.

In Chemical Formulas 2A and 2B, $X^1$, $X^2$, $X^3$, and $X^4$ may be sulfur (S).

$R^1$ and $R^2$ may be linked to each other to provide a $C_6$-aryl ring fused with an $X^3$-containing ring, or $R^4$ and $R^5$ may be linked to each other to provide a $C_6$-aryl ring fused with an $X^4$-containing ring.

Such a fused polycyclic heteroaromatic compound may be a fused polycyclic heteroaromatic compound represented by the following Chemical Formula 3A or 3B.

[Chemical Formula 3A]

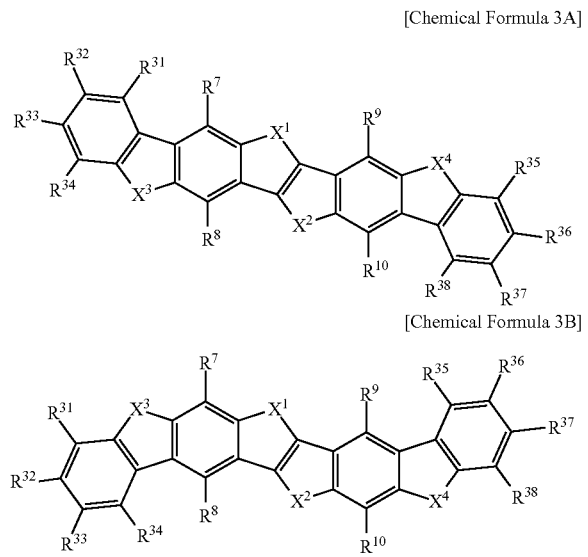

[Chemical Formula 3B]

In Chemical Formulas 3A and 3B,
$X^1$, $X^2$, $X^3$, $X^4$, $R^7$, $R^8$, $R^9$, and $R^{10}$ are the same as in Chemical Formulas 1A and 1B, $R^{31}$ to $R^{38}$ are each independently hydrogen, a halogen (—F, —Cl, —Br, or —I), a substituted or unsubstituted linear or branched C1 to C30 alkyl group, for example a substituted or unsubstituted linear or branched C1 to C20 alkyl group, a substituted or unsubstituted linear or branched C2 to C30 alkenyl group, for example a substituted or unsubstituted linear or branched C2 to C20 alkenyl group, a substituted or unsubstituted linear or branched C2 to C30 alkynyl group, for example a substituted or unsubstituted linear or branched C2 to C20 alkynyl group, a substituted or unsubstituted C7 to C30 arylalkyl group, for example a substituted or unsubstituted C7 to C20 arylalkyl group, a substituted or unsubstituted C2 to C30 heteroarylalkyl group, for example a substituted or unsubstituted C2 to C20 heteroarylalkyl group, a substituted or unsubstituted C2 to C30 alkylheteroaryl group, for example a substituted or unsubstituted C2 to C20 alkylheteroaryl group, a substituted or unsubstituted C5 to C30 cycloalkyl group, for example a substituted or unsubstituted C5 to C20 cycloalkyl group, a substituted or unsubstituted C2 to C30 heterocycloalkyl group, for example a substituted or unsubstituted C2 to C20 heterocycloalkyl group, a substituted or unsubstituted C6 to C30 aryl group, for example a substituted or unsubstituted C6 to C20 aryl group, or a substituted or unsubstituted C2 to C30 heteroaryl group, for example a substituted or unsubstituted C2 to C20 heteroaryl group, or two selected from $R^{31}$ to $R^{34}$ or two selected from $R^{35}$ to $R^{38}$ may be linked to the adjacent functional group to provide an aromatic ring, a heteroaromatic ring, or an alicyclic ring fused with the $C_6$-aryl ring.

In Chemical Formulas 3A and 3B, $X^1$, $X^2$, $X^3$, and $X^4$ may be sulfur (S).

The fused polycyclic heteroaromatic compound may be a fused polycyclic heteroaromatic compound represented by the following Chemical Formula 4A or 4B.

[Chemical Formula 4A]

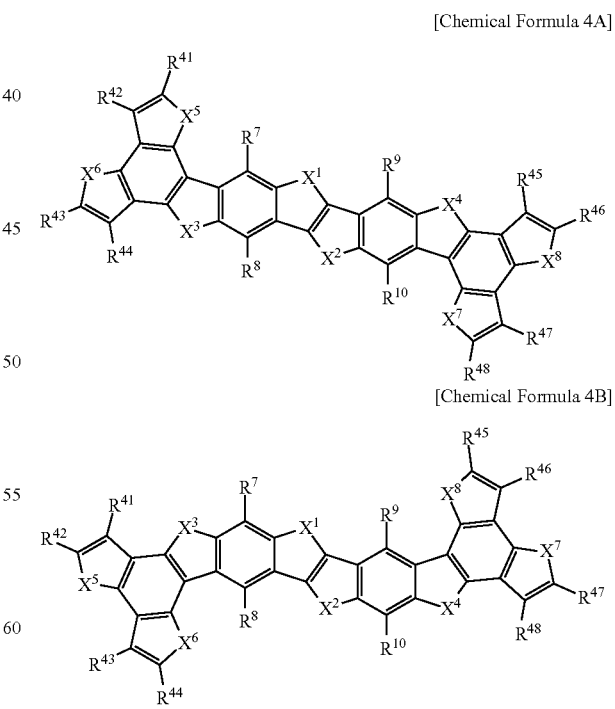

[Chemical Formula 4B]

In Chemical Formulas 4A and 4B,
$X^1$, $X^2$, $X^3$, $X^4$, $R^7$, $R^8$, $R^9$, and $R^{10}$ are the same as in Chemical Formulas 1A and 1B, X⁵ to X⁸ are each independently O, S, Se, Te, N—$R^a$, or $CR^bR^c$, wherein $R^a$ to $R^c$ are each independently hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example a C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—C(=O)$R^{13}$, wherein $R^{13}$ is a substituted or unsubstituted C1 to C30 alkyl group, for example a C1 to C20 alkyl group), a sulfonyl group (—S(=O)$R^{14}$, wherein $R^{14}$ is a substituted or unsubstituted C1 to C30 alkyl group, for example a C1 to C20 alkyl group), or a carbamate group (—$NH_2COOR^{15}$, wherein $R^{15}$ is a substituted or unsubstituted C1 to C30 alkyl group, for example a C1 to C20 alkyl group), $R^{41}$ to $R^{48}$ are each independently hydrogen, a halogen, a substituted or unsubstituted linear or branched C1 to C30 alkyl group, for example a substituted or unsubstituted linear or branched C1 to C20 alkyl group, a substituted or unsubstituted linear or branched C2 to C30 alkenyl group, for example a substituted or unsubstituted linear or branched C2 to C20 alkenyl group, a substituted or unsubstituted linear or branched C2 to C30 alkynyl group, for example a substituted or unsubstituted linear or branched C2 to C20 alkynyl group, a substituted or unsubstituted C7 to C30 arylalkyl group, for example a substituted or unsubstituted C7 to C20 arylalkyl group, a substituted or unsubstituted C2 to C30 heteroarylalkyl group, for example a substituted or unsubstituted C2 to C20 heteroarylalkyl group, a substituted or unsubstituted C2 to C30 alkylheteroaryl group, for example a substituted or unsubstituted C2 to C20 alkylheteroaryl group, a substituted or unsubstituted C5 to C30 cycloalkyl group, for example a substituted or unsubstituted C5 to C20 cycloalkyl group, a substituted or unsubstituted C2 to C30 heterocycloalkyl group, for example a substituted or unsubstituted C2 to C20 heterocycloalkyl group, a substituted or unsubstituted C6 to C30 aryl group, for example a substituted or unsubstituted C6 to C20 aryl group, or a substituted or unsubstituted C2 to C30 heteroaryl group, for example a substituted or unsubstituted C2 to C20 heteroaryl group, or at least one pair of substituents selected from $R^{41}$ and $R^{42}$, $R^{43}$ and $R^{44}$, $R^{45}$ and $R^{46}$, and $R^{47}$ and $R^{48}$ may be linked to each other to provide an aromatic ring, a heteroaromatic ring, or an alicyclic ring fused with at least one of a $X^5$-containing ring, a $X^6$-containing ring, a $X^7$-containing ring, and a $X^8$-containing ring.

In Chemical Formulas 4A and 4B, $X^1$, $X^2$, $X^3$, $X^4$, $X^5$, $X^6$, $X^7$, and $X^8$ may be sulfur (S).

The fused polycyclic heteroaromatic compound may be a fused polycyclic heteroaromatic compound represented by the following Chemical Formula 5A or 5B.

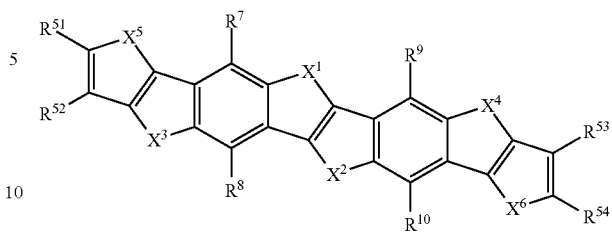

[Chemical Formula 5A]

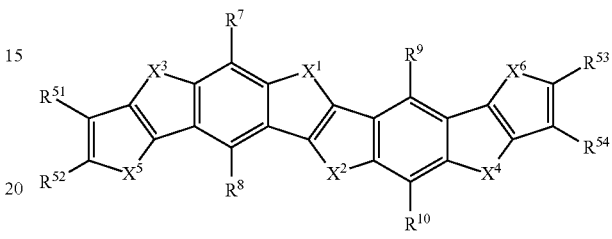

[Chemical Formula 5B]

In Chemical Formulas 5A and 5B, $X^1$, $X^2$, $X^3$, $X^4$, $R^7$, $R^8$, $R^9$, and $R^{10}$ are the same as in Chemical Formulas 1A and 1B, $X^5$ and $X^6$ are each independently O, S, Se, Te, N—$R^a$, or $CR^bR^c$, wherein $R^a$ to $R^c$ are each independently hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example a C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—C(=O)$R^{13}$, wherein $R^{13}$ is a substituted or unsubstituted C1 to C30 alkyl group, for example a C1 to C20 alkyl group), a sulfonyl group (—S(=O)$R^{14}$, wherein $R^{14}$ is a substituted or unsubstituted C1 to C30 alkyl group, for example a C1 to C20 alkyl group), or a carbamate group (—$NH_2COOR^{15}$, wherein $R^{15}$ is a substituted or unsubstituted C1 to C30 alkyl group, for example a C1 to C20 alkyl group), and $R^{51}$ to $R^{54}$ are each independently hydrogen, a halogen, a substituted or unsubstituted linear or branched C1 to C30 alkyl group, for example a substituted or unsubstituted linear or branched C1 to C20 alkyl group, a substituted or unsubstituted linear or branched C2 to C30 alkenyl group, for example a substituted or unsubstituted linear or branched C2 to C20 alkenyl group, a substituted or unsubstituted linear or branched C2 to C30 alkynyl group, for example a substituted or unsubstituted linear or branched C2 to C20 alkynyl group, a substituted or unsubstituted C7 to C30 arylalkyl group, for example a substituted or unsubstituted C7 to C20 arylalkyl group, a substituted or unsubstituted C2 to C30 heteroarylalkyl group, for example a substituted or unsubstituted C2 to C20 heteroarylalkyl group, a substituted or unsubstituted C2 to C30 alkylheteroaryl group, for example a substituted or unsubstituted C2 to C20 alkylheteroaryl group, a substituted or unsubstituted C5 to C30 cycloalkyl group, for example a substituted or unsubstituted C5 to C20 cycloalkyl group, a substituted or unsubstituted C2 to C30 heterocycloalkyl group, for example a substituted or unsubstituted C2 to C20 heterocycloalkyl group, a substituted or unsubstituted C6 to C30 aryl group, for example a substituted or unsubstituted C6 to C20 aryl group, or a substituted or unsubstituted C2 to C30 heteroaryl group, for example a substituted or unsubstituted C2 to C20 heteroaryl group, or at least one pair of substituents selected from $R^{51}$ and $R^{52}$, and $R^{53}$ and $R^{54}$, may be linked to each other to provide an aromatic ring, a heteroaromatic ring, or an alicyclic ring fused with a $X^5$-containing ring or fused with a $X^6$-containing ring.

In Chemical Formulas 5A and 5B, $X^1$, $X^2$, $X^3$, $X^4$, $X^5$, and $X^6$ may be sulfur (S).

Examples of the fused polycyclic heteroaromatic compound may include the following compounds (1) to (9).

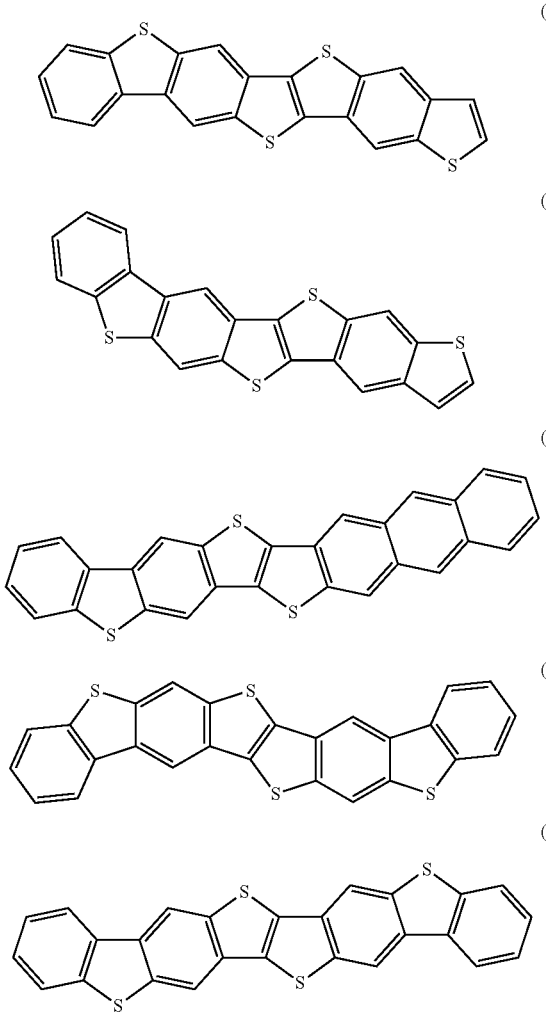

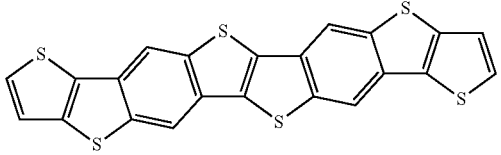

(6)

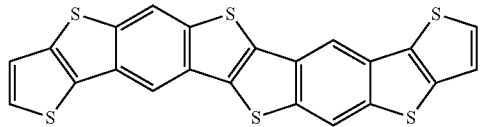

(7)

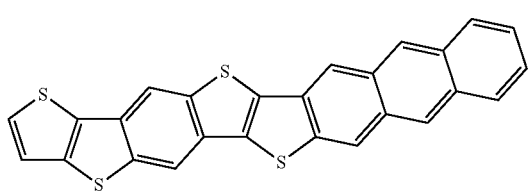

(8)

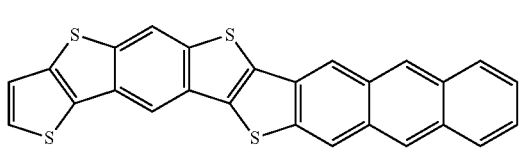

(9)

The aromatic rings of the compounds (1) to (9) may be substituted with a substitutent, for example C1 to C30 linear or branched alkyl group.

The reorganization energy of compounds (1), (3), (7), (8), and (9) among the compounds (1) to (9) is calculated by using the Gaussian 03 program in DFT B3PW91 6-311G+ (d,p) level, and the results are shown in the following Table 1. For comparison, the reorganization energy of the following compounds ref-1 and ref-2 is also shown in Table 1.

TABLE 1

| Compound | λ1 (eV) | λ2 (eV) | λ+ (eV) |
|---|---|---|---|
| Compound ref-1 | 0.073 | 0.062 | 0.135 |
| Compound ref-2 | 0.083 | 0.079 | 0.162 |
| Compound (1) | 0.080 | 0.074 | 0.154 |
| Compound (3) | 0.056 | 0.057 | 0.113 |
| Compound (7) | 0.064 | 0.059 | 0.123 |
| Compound (8) | 0.060 | 0.059 | 0.119 |
| Compound (9) | 0.056 | 0.059 | 0.115 |

In Table 1, λ1 refers to reorganization energy in the ground state, λ2 refers to reorganization energy in the charged state, and λ+ refers to the sum of two reorganization energies. As shown in Table 1, compounds (1), (3), (7), (8), and (9) have lower reorganization energies than compound ref-2, with compounds (3), (7), (8), and (9) having lower reorganization energies than compounds ref-1 and ref-2.

The fused polycyclic heteroaromatic compound may be prepared according to a general method, for example, chemical or electrochemical oxidation synthesis, which is a representative method of polymerizing an aromatic group or a heteroaromatic group, or condensation polymerization using a compound of an organic transition element such as nickel or palladium.

The compound represented by Chemical Formula 1A may be prepared by cyclizing an intermediate compound represented by Chemical Formula 1A-1 or 1A-2 in which an $X^3$-containing ring or an $X^4$-containing ring is introduced at both terminal ends of a thieno[3,2-b]thiophene positioned in the center. The cyclization reaction may be performed by the method described in, for example, J. Org. Chem. 2005, 70, 4502-4505.

[Chemical Formula 1A-1]

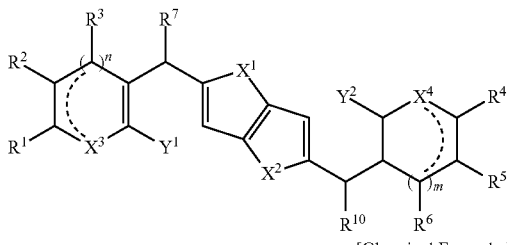

[Chemical Formula 1A-2]

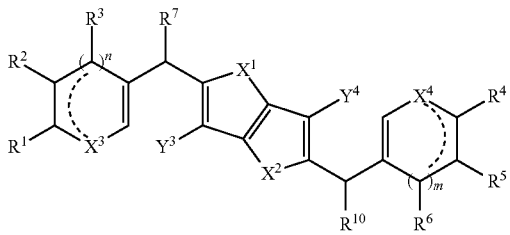

In Chemical Formulas 1A-1 and 1A-2, $X^1$, $X^2$, $X^3$, $X^4$, $R^1$, $R^2$, $R^3$, $R^4$, $R^5$, $R^6$, $R^7$, and $R^{10}$ are the same as in Chemical Formula 1A; $Y^1$ and $Y^3$ are carbonyl groups (—C(=O)$R^8$, wherein $R^8$ is the same as in Chemical Formula 1A) or a halogen (e.g., —Br); and $Y^2$ and $Y^4$ are carbonyl groups (—C(=O)$R^9$, wherein $R^9$ is the same as in Chemical Formula 1A) or a halogen (e.g., —Br). For example, in Chemical Formula 3A, the fused polycyclic heteroaromatic compound in which $X^1$, $X^2$, $X^3$, and $X^4$ are S, and $R^7$, $R^8$, $R^9$, $R^{10}$, and $R^{31}$ to $R^{38}$ are hydrogens, may be synthesized according to the following Reaction Scheme 1, but is not specifically limited thereto.

[Reaction Scheme 1]

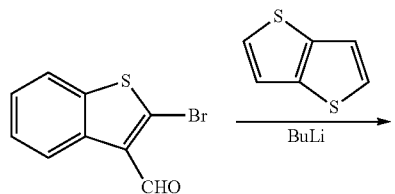

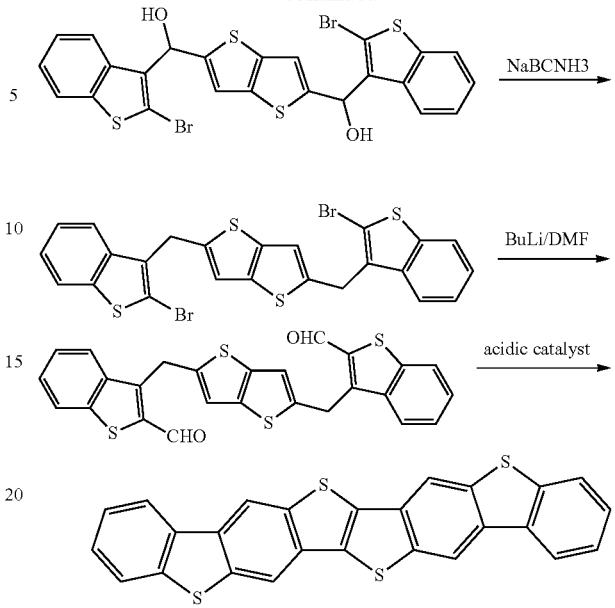

Reaction Scheme 1 may be performed using a heteroaromatic ring compound substituted with bromine and/or lithium, etc. at about −78° C. to room temperature (about 23° C. to about 25° C.) in an air or nitrogen atmosphere. The solvent may include the commonly used toluene, dimethyl formamide (DMF), N-methylpyrrolidinone (NMP), tetrahydrofuran (THF), or the like. The catalyst for dehydration in the last step may be an acidic catalyst such as Amberlyst 15 or the like.

The molecular weight of the fused polycyclic heteroaromatic compound obtained from the synthesis may be adjusted depending upon the usage and the case. For example, the molecular weight may be between about 350 to about 3000.

An organic thin film may include the fused polycyclic heteroaromatic compound, and an electronic device may include the organic thin film.

The organic thin film may include the fused polycyclic heteroaromatic compound. As a result, the organic thin film may be applied to an organic semiconductor layer for an electronic device, or a carrier transport layer such as a channel layer. The electronic device including the same may have desirable electrical properties such as high charge mobility as well as improved processibility and workability.

The organic thin film may be prepared by dissolving at least one kind of the fused polycyclic heteroaromatic compounds in an organic solvent and depositing the same on a substrate according to the general method, or coating the same at room temperature according to a solution process. If required, heating treatment may be performed after the deposition or coating process to further enhance the densification and uniformity of the thin film.

The organic solvent may include at least one kind of general organic solvent, for example, at least one kind of an aliphatic hydrocarbon solvent such as hexane, heptane, or the like; an aromatic hydrocarbon solvent such as toluene, pyridine, quinoline, anisole, mesitylene, xylene, or the like; a ketone-based solvent such as methyl isobutyl ketone, 1-methyl-2-pyrrolidinone, cyclohexanone, acetone, or the like; an ether-based solvent such as tetrahydrofuran, isopropyl ether, or the like; an acetate-based solvent such as ethyl acetate, butyl acetate, propylene glycol methyl ether acetate, or the like; an alcohol-based solvent such as isopropyl alcohol, butanol, or the like; an amide-based solvent such as dimethyl acetamide, dimethyl formamide, or the like; silicone-based solvent; and a mixture of solvents. The amount of the fused polycyclic heteroaromatic compound dissolved in the organic solvent may be adequately selected and determined by a person of ordinary skill in the art. For example, the amount of the fused polycyclic heteroaromatic compound may be present in a range of about 0.01 wt % to about 50 wt % with regard to the solvent, depending on the solubility and coating property.

The method of providing an organic thin film may include thermal deposition, vacuum deposition, laser deposition, screen printing, printing, imprinting, spin casting, dipping, inkjetting, roll coating, flow coating, drop casting, spray coating, roll printing, or the like, but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent. For example, the thickness may be in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, a sensor, or the like, and the organic thin film may be applied to each device according to the general process commonly known in the art.

For example, the transistor includes a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by applying a composition including the fused polycyclic heteroaromatic compound to a solution process such as screen printing, printing, spin coating, dipping, inkjetting, or the like. When the active layer is formed by the solution process, the process cost may be reduced, and a wide area device may be effectively fabricated.

Figure 2:
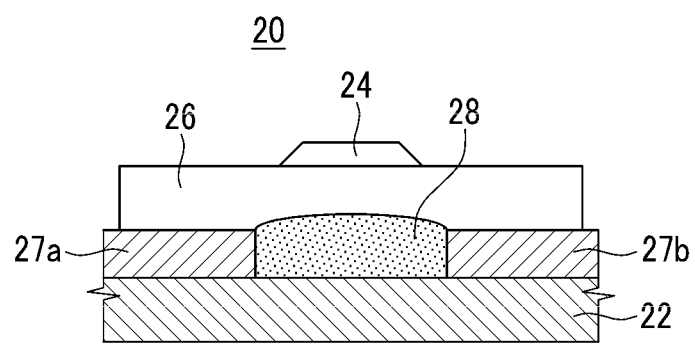
FIG. 2 is a schematic cross-sectional view of another transistor according to example embodiments.

FIGS. 1 and 2 are schematic cross-sectional views showing a transistor according to example embodiments. The transistor may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. On the insulation layer 16, a source electrode 17a and a drain electrode 17b defining a channel region are provided, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic such as polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or metal.

In addition, the gate electrodes 14 and 24, source electrodes 17a and 27a, and drain electrodes 17b and 27b may include a generally-used metal, for example, gold (Au), silver (Ag), aluminum (Al), nickel (Ni), or indium tin oxide (ITO), but it is not limited thereto.

The insulation layers 16 and 26 may include a generally-used insulator having a high dielectric constant, for example, a ferroelectric insulator such as $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator such as $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$, AlON, and so on; or an organic insulator such as polyimide, benzocyclobutane (BCB), parylene, polyacrylate, polyvinyl alcohol, polyvinylphenol, and so on, but it is not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

Hereinafter, various embodiments are illustrated in more detail with reference to the following examples. However, it should be understood that the following are merely example embodiments and are not intended to be limiting.

EXAMPLES

Example 1

Synthesis of Fused Polycyclic Heteroaromatic Compound

[Reaction Scheme 2]

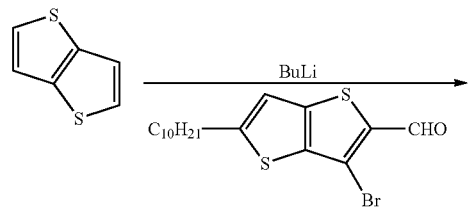

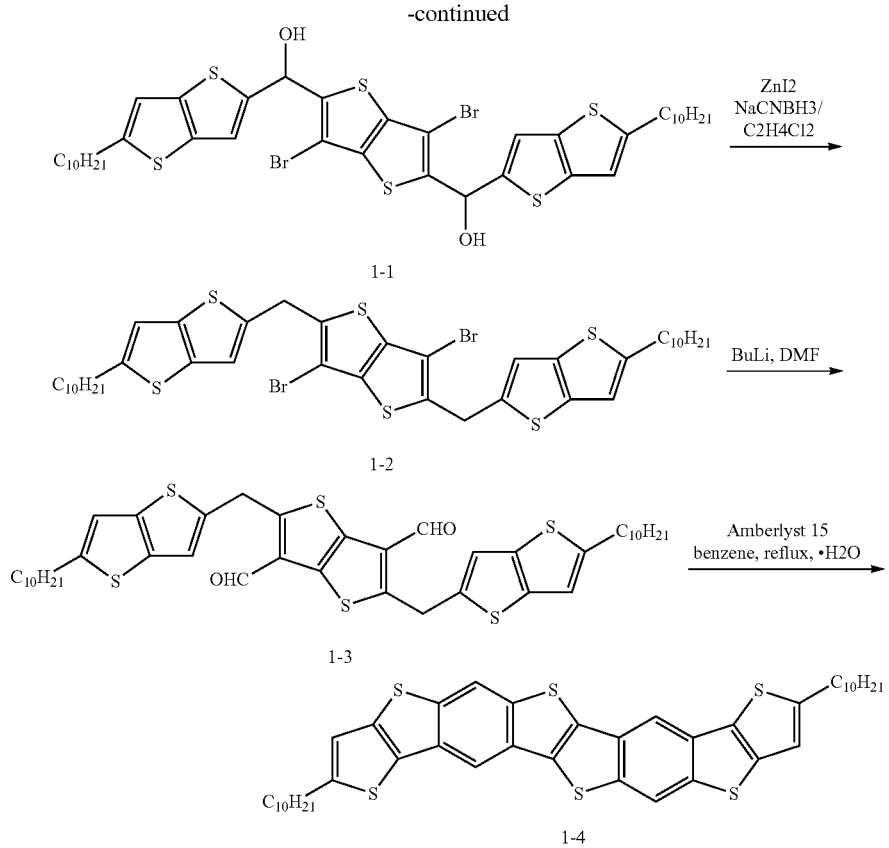

Synthesis of Compound 1-1

1.27 g (9 mmol) of thieno[3,2:b]thiophene is dissolved in 50 mL dry ether, and the resultant is added in dropwise fashion to 100 mL of dry ether solution in which 8 mL of 2.5M butyl lithium solution dissolved in hexane is contained and is cooled to 0° C. The temperature is slowly increased to room temperature (24° C.) and agitation for two hours is performed at room temperature. 7 g (18 mmol) of 2'-decyl-3-bromo-thieno[3,2:b]-thiophene-2-aldehyde is slowly added in a dropwise fashion to the resultant haze solution and is agitated overnight. 50 mL of ammonium chloride saturated solution is added. Precipitated materials are filtered and the filtered product is washed with water and ether to a Compound 1-1 (yield: 75%).

$^1$H NMR (300 MHz, CDCl$_3$): δ ppm 7.15 (d, 2H), 6.83 (d, 2H), 6.33 (d, 2H), 2.81 (t, 4H), 2.59 (d, 2H), 1.68 (m, 4H), 1.30 (m, 28H), 0.88 (t, 6H); $^{13}$C NMR (75.5 MHz, CDCl$_3$): δ ppm 149.3, 146.3, 138.1, 137.6, 134.4, 133.3, 117.3, 116.2, 115.6, 108.4, 68.7, 31.9, 31.4, 30.8, 29.6, 29.5, 29.3, 29.1, 22.7, 14.1.

Synthesis of Compound 1-2

1.78 g (1.94 mmol) of the Compound 1-1 is dissolved in 150 mL of dichloromethane and 2 g (6.2 mmol) of ZnI$_2$ and 1.8 g (27 mmol) of NaCNBH$_3$ are slowly added. The resultant is agitated at room temperature for 24 hours, and is filtered through a Celite pad. The filtered solution is washed with ammonium chloride saturated solution and water respectively, and dried with MgSO$_4$ followed by concentration in a reduced pressure to obtain yellow oil. The yellow oil is purified by using a silica chromatography to obtain a Compound 1-2 (yield: 80%).

$^1$H NMR (300 MHz, CDCl$_3$): δ ppm 6.99 (s, 2H), 6.81 (s, 2H), 4.22 (s, 4H), 2.78 (t, 4H), 1.63 (m, 4H), 1.27 (m, 28H), 0.88 (t, 6H); $^{13}$C NMR (75.5 MHz, CDCl$_3$): 6 ppm 148.0, 141.1, 137.5, 136.6, 135.8, 131.3, 118.2, 116.2, 109.2, 31.9, 31.4, 30.9, 30.5, 29.6, 29.5, 29.3, 29.1, 22.7, 14.1.

Synthesis of Compound 1-3

4.1 mmol of t-butyl lithium is dissolved in 50 mL of tetrahydrofuran (THF) and cooled to −78° C. 0.8 g (0.9 mmol) of the compound 1-2 dissolved in 50 mL of THF is slowly added in a dropwise fashion. The resultant is agitated at −78° C. for about 30 minutes, and 2 mL of dimethylform amide (DMF) is added followed by agitating it for about 2 hours. Water is poured to terminate a reaction and then 100 mL of ethyl acetate is added. The resultant is washed with water and brine and an organic layer is dried with MgSO$_4$ followed by concentration in a reduced pressure to obtain colorless oil. The colorless oil is purified by using a silica chromatography to obtain a Compound 1-3 (yield: 70%).

$^1$H NMR (300 MHz, CDCl$_3$): δ ppm 10.1 (s, 2H), 7.02 (s, 2H), 6.97 (s, 2H), 4.63 (s, 4H), 2.83 (t, 4H), 1.55 (m, 4H), 1.28 (m, 28H), 0.88 (t, 6H); $^{13}$C NMR (75.5 MHz, CDCl$_3$): δ ppm 182.1, 156.1, 145.0, 141.3, 140.3, 139.2, 137.8, 137.6, 118.7, 117.2, 31.9, 31.6, 31.2, 29.6, 29.5, 29.3, 29.3, 29.27, 22.7, 14.1.

Synthesis of Compound 1-4

0.45 g of the Compound 1-3 is dissolved in 30 mL of benzene, and 0.6 g of Amberlyst 15 is added. The resulting mixture is agitated while refluxing and water is removed using Dean-Stark trap. After 24 hours, a yellow solid is precipitated. A temperature is lowered to room temperature and Amberlyst 15 is precipitated. Floating materials are removed followed by filtering to obtain a yellow solid, Compound 1-4 (yield: 60%).

$^1$H NMR (300 MHz, CDCl$_3$): δ ppm 8.17 (s, 2H), 8.16 (s, 2H), 7.09 (s, 2H), 2.94 (t, 4H), 1.76 (m, 4H), 1.24 (m, 28H), 0.88 (t, 6H).

Example 2

Synthesis of Fused Polycyclic Heteroaromatic Compound

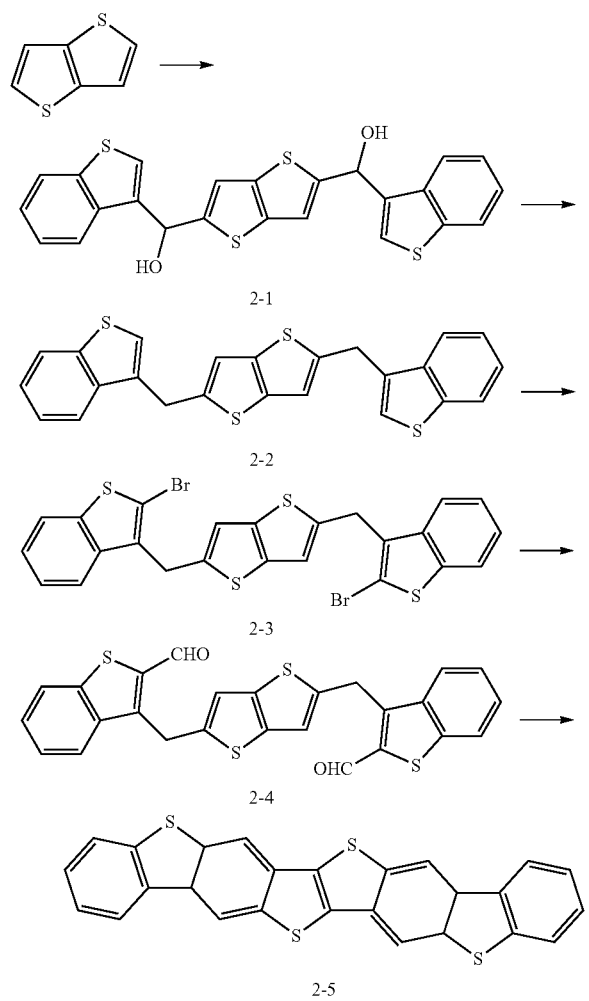

Synthesis of Compound 2-1

4.22 g (30 mmol) of thieno[3,2:b]thiophene is dissolved in 50 mL of dry ether, and the resultant is added in dropwise fashion to 100 mL of dry ether solution in which 25 mL of 2.5M butyl lithium solution dissolved in hexane is contained and is cooled to 0° C. The temperature is slowly increased to room temperature (24° C.) and agitation for two hours is performed at room temperature. 10 g (62 mmol) of benzothiophene-3-aldehyde is slowly added in a dropwise fashion to the resultant haze solution and is agitated overnight. 100 mL of ammonium chloride saturated solution is added. Precipitated materials are filtered and the filtered product is washed with water and ether to a Compound 2-1 (yield 70%).

$^1$H NMR (300 MHz, CDCl$_3$): δ ppm 7.89 (m, 2H), 7.77 (m, 2H), 7.59 (s, 2H), 7.35 (m, 4H), 7.13 (s, 2H), 6.44 (d, 2H), 2.56 (d, 2H).

Synthesis of Compound 2-2

8.8 g (19 mmol) of the Compound 2-1 is dissolved in 300 mL of dichloromethane and 19 g (61 mmol) of ZnI$_2$ and 17 g (270 mmol) of NaCNBH$_3$ are slowly added. The resultant is agitated at room temperature for 24 hours, and is filtered through a Celite pad. The filtered solution is washed with ammonium chloride saturated solution and water respectively, and dried with MgSO$_4$ followed by concentration in a reduced pressure to obtain yellow oil. The yellow oil is purified by using a silica chromatography to obtain a Compound 2-2 (yield: 75%).

$^1$H NMR (300 MHz, CDCl$_3$): δ ppm 7.84 (m, 2H), 7.74 (m, 2H), 7.35 (m, 4H), 7.21 (s, 2H), 6.91 (s, 2H), 4.40 (s, 4H).

Synthesis of Compound 2-3

1.1 g (2.5 mmol) of the compound 2-1 is dissolved in 50 mL of chloroform. 0.9 g, 5 mmol of N-bromosuccinimide (NBS) is added, and then is agitated at room temperature for 24 hours. The mixture is filtered through a Celite pad. The filtered solution is dried with MgSO$_4$ followed by concentration in a reduced pressure and separation using a silica gel column chromatography (chloroform:hexane).

$^1$H NMR (300 MHz, CDCl$_3$): δ ppm 7.87 (m, 2H), 7.75 (m, 2H), 7.37 (m, 4H), 7.24 (s, 2H), 4.41 (s, 4H).

Synthesis of Compound 2-4

4.0 mmol of t-butyl lithium is dissolved in 50 mL of tetrahydrofuran (THF) and cooled to −78° C. 0.6 g (1 mmol) of the compound 1-3 dissolved in 100 mL of THF is slowly added in a dropwise fashion. The resultant is agitated at −78° C. for about 1 hour, and 1 mL of dimethylformamide (DMF) is added followed by agitating it for about 1 hour. Water is poured to terminate a reaction and then 100 mL of ethyl acetate is added. The resultant is washed with water and brine and an organic layer is dried with MgSO$_4$ followed by concentration in a reduced pressure to obtain colorless oil. The colorless oil is purified by using a silica chromatography to obtain a Compound 2-4 (yield: 60%).

$^1$H NMR (300 MHz, CDCl$_3$): δ ppm 10.1 (s, 2H), 7.88 (m, 2H), 7.76 (m, 2H), 7.36 (m, 4H), 7.26 (s, 2H), 4.42 (s, 4H).

Synthesis of Compound 2-5

0.40 g of the Compound 2-4 is dissolved in 30 mL of benzene, and 0.5 g of Amberlyst 15 is added. The resulting mixture is agitated while refluxing and water is removed using Dean-Stark trap. After 24 hours, a yellow solid is precipitated. A temperature is lowered to room temperature and Amberlyst 15 is precipitated. Floating materials are removed followed by filtering to obtain a yellow solid, Compound 2-5 (yield: 50%).

$^1$H NMR (300 MHz, CDCl$_3$): MR (308.25 (s, 2H), 8.11 (s, 2H), 7.90 (m, 2H), 7.78 (m, 2H), 7.39 (m, 4H).

Example 3

Manufacturing Organic Thin Film Transistor (OTFT)

A gate electrode of chromium is deposited at 1000 Å on a cleaned glass substrate by sputtering, and an insulation layer of $SiO_2$ is deposited thereon at 3000 Å by a CVD method. Then Au is deposited at 700 Å thereon by sputtering to provide a source electrode and a drain electrode. The glass substrate is washed for 10 minutes using isopropyl alcohol, and dried before coating the organic semiconductor material. In addition, the insulation layer of $SiO_2$ is treated with $UV/O_3$ for 30 minutes before the surface modification.

The device is dipped in an octyltrichloro silane solution that is diluted in n-hexane at a concentration of 10 mM for 30 minutes, and it is washed with hexane and alcohol and then dried. The compound obtained from Example 1 is thermally deposited under a vacuum of about $5 \times 10^{-6}$ torr at about 0.2 Å/sec to provide an active layer 18 having a thickness of about 1000 Å. Accordingly, an OTFT device 10 having a structure shown in FIG. 1 is obtained.

Figure 3:
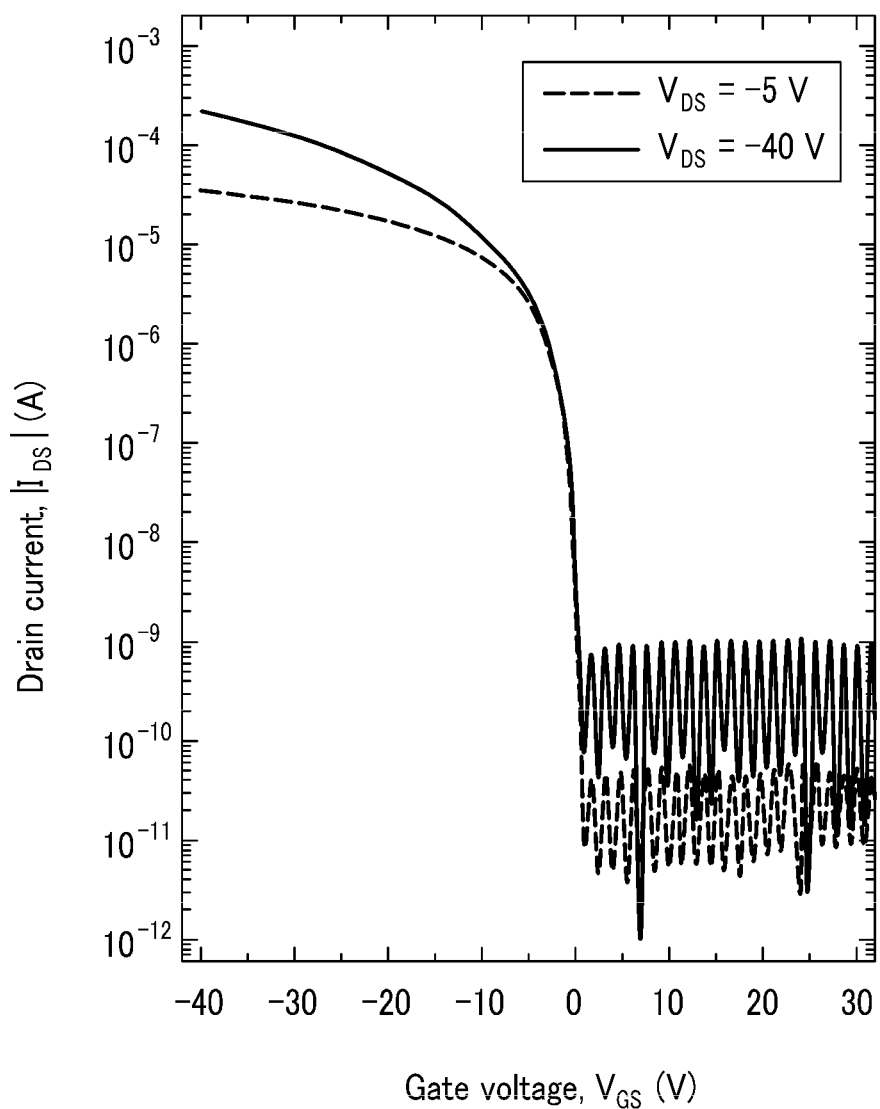
FIG. 3 is a graph showing current-transfer characteristics of the organic thin film transistor (OTFT) device according to Example 3.

Furthermore, the OTFT device according to Example 3 was measured for current-transfer characteristics using a semiconductor characterization system (4200-SCS, KEITHLEY CORP.). The result is shown in FIG. 3. As shown in FIG. 3, the OTFT device according to Example 3 shows stable current-transfer characteristics.

While this disclosure has been described in connection with various example embodiments, it is to be understood that the examples are not limited to the disclosed embodiments, but, on the contrary, are intended to cover various modifications and equivalent arrangements included within the spirit and scope of the appended claims.

<Description of Symbols>

| | |
|---|---|
| 10, 20: transistor | 12, 22: substrate |
| 16, 26: insulation layer | 18, 28: active layer |
| 14, 24: gate electrode | 17a, 27a: source electrode |
| 17b, 27b: drain electrode | |

What is claimed is:

1. A fused polycyclic heteroaromatic compound represented by the following Chemical Formula 2A or 2B,

[Chemical Formula 2A]

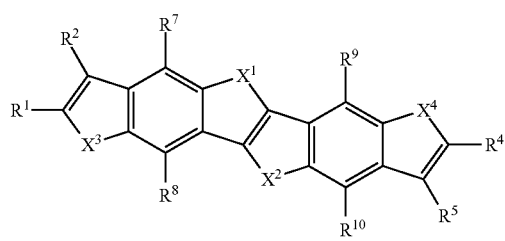

[Chemical Formula 2B]

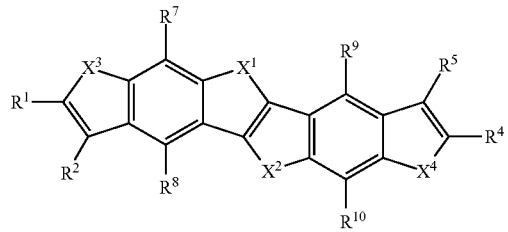

wherein, in Chemical Formulas 2A and 2B, $X^1$ and $X^2$ are each independently O, S, Se, Te, or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, $X^3$ and $X^4$ are each independently O, S, Se, Te, N, N—$R^a$, or $CR^b$, (wherein $R^a$ and $R^b$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, provided that $X^3$ and $X^4$ are not simultaneously $CR^b$, $R^1$, $R^2$, $R^4$, $R^5$, $R^7$, $R^8$, $R^9$, and $R^{10}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkenyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group or substituted or unsubstituted C2 to C30 heteroaryl group, a heteroaromatic ring, or an alicyclic ring fused with a $X^3$-containing ring, and $R^1$ and $R^2$ are linked to provide the aromatic ring, the heteroaromatic ring, or the alicyclic ring fused with the $X^3$-containing ring, or $R^4$ and $R^5$ are linked to provide the aromatic ring, the heteroaromatic ring, or the alicyclic ring fused with the $X^4$-containing ring.

2. The fused polycyclic heteroaromatic compound of claim 1, wherein $X^1$, $X^2$, $X^3$, and $X^4$ are sulfur (S).

3. A fused polycyclic heteroaromatic compound represented by the following Chemical Formula 3A or 3B,

[Chemical Formula 3A]

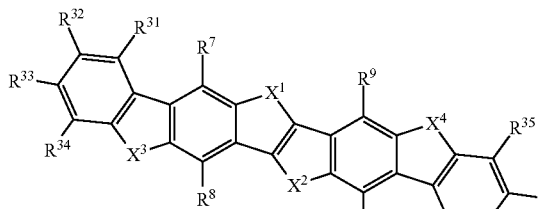

[Chemical Formula 3B]

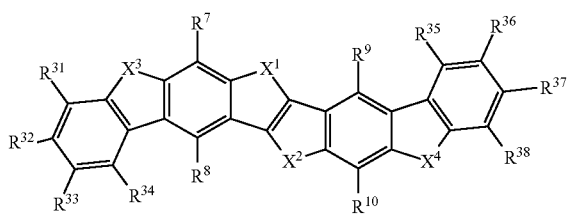

wherein, in Chemical Formulas 3A and 3B, $X^1$ and $X^2$ are each independently O, S, Se, Te, or N—$^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, $X^3$ and $X^4$ are each independently O, S, Se, Te, N, N—$R^a$, or $CR^b$, (wherein $R^a$ and $R^b$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, provided that $X^3$ and $X^4$ are not simultaneously $CR^b$, $R^7$, $R^8$, $R^9$, and $R^{10}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkenyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group or substituted or unsubstituted C2 to C30 heteroaryl group, $R^{31}$ to $R^{38}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group or substituted or unsubstituted C2 to C30 heteroaryl group, or two selected from $R^{31}$ to $R^{34}$ or two selected from $R^{35}$ to $R^{38}$ are linked to an adjacent functional group to provide an aromatic ring, a heteroaromatic ring, or an alicyclic ring fused with a $C_6$-aryl ring.

4. The fused polycyclic heteroaromatic compound of claim 3, wherein $X^1$, $X^2$, $X^3$, and $X^4$ are sulfur (S).

5. A fused polycyclic heteroaromatic compound represented by the following Chemical Formula 4A or 4B,

[Chemical Formula 4A]

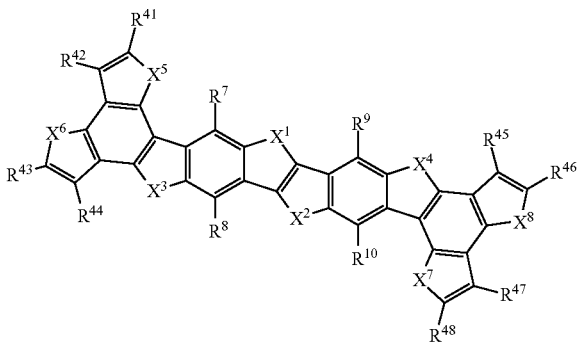

[Chemical Formula 4B]

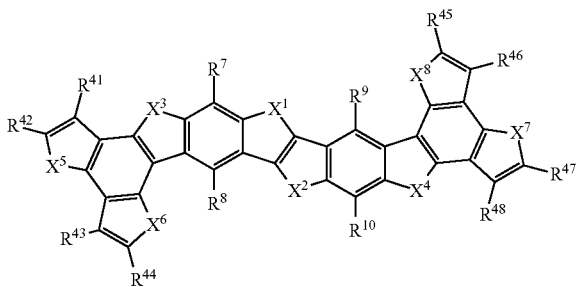

wherein, in Chemical Formulas 4A and 4B, $X^1$ and $X^2$ are each independently O, S, Se, Te, or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, $X^3$ and $X^4$ are each independently O, S, Se, Te, N, N—$R^a$, or $CR^b$, (wherein $R^a$ and $R^b$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, provided that $X^3$ and $X^4$ are not simultaneously $CR^b$, $R^7$, $R^8$, $R^9$, and $R^{10}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group or substituted or unsubstituted C2 to C30 heteroaryl group, and $X^5$ to $X^8$ are each independently O, S, Se, Te, N—$R^a$, or $CR^bR^c$, wherein $R^a$ to $R^c$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, and $R^{41}$ to $R^{48}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, or at least one pair of substituents selected from $R^{41}$ and $R^{42}$, $R^{43}$ and $R^{44}$, $R^{45}$ and $R^{46}$, and $R^{47}$ and $R^{48}$ is linked to provide an aromatic ring, a heteroaromatic ring, or an alicyclic ring fused with at least one of a $X^5$-containing ring, a $X^6$-containing ring, a $X^7$-containing ring, and a $X^8$-containing ring.

6. The fused polycyclic heteroaromatic compound of claim 5, wherein $X^1$, $X^2$, $X^3$, $X^4$, $X^5$, $X^6$, $X^7$, and $X^8$ are sulfur (S).

7. A fused polycyclic heteroaromatic compound represented by the following Chemical Formula 5A or 5B,

[Chemical Formula 5A]

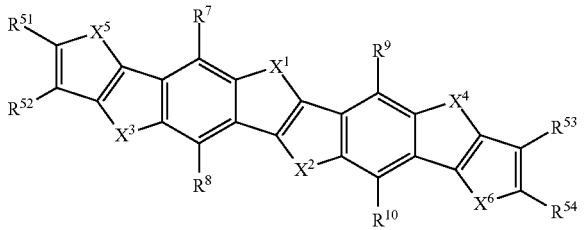

-continued

[Chemical Formula 5B]

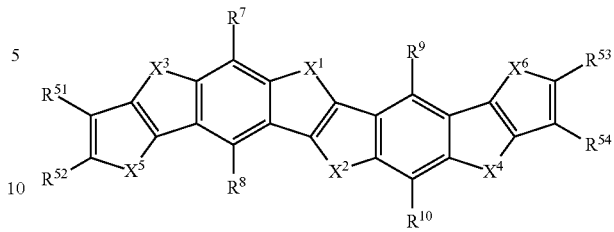

wherein, in Chemical Formulas 5A and 5B, $X^1$ and $X^2$ are each independently O, S, Se, Te, or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, $X^3$ and $X^4$ are each independently O, S, Se, Te, N, N—$R^a$, or $CR^b$, (wherein $R^a$ and $R^b$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, provided that $X^3$ and $X^4$ are not simultaneously $CR^b$, $R^7$, $R^8$, $R^9$, and $R^{10}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkenyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group or substituted or unsubstituted C2 to C30 heteroaryl group, and $X^5$ and $X^6$ are each independently O, S, Se, Te, N—$R^a$, or $CR^bR^c$, wherein $R^a$ to $R^c$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group, a substituted or unsubstituted C4 to C30 cycloalkyl group, a substituted or unsubstituted C4 to C30 cycloalkyloxy group, a substituted or unsubstituted C2 to C30 heteroaryl group, an acyl group, a sulfonyl group, or a carbamate group, and $R^{51}$ to $R^{54}$ are each independently hydrogen, a halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, or at least one pair of substituents selected from $R^{51}$ and $R^{52}$, and $R^{53}$ and $R^{54}$, is linked to provide an aromatic ring, a heteroaromatic ring, or an alicyclic ring fused with a $X^5$-containing ring or fused with a $X^6$-containing ring.

8. The fused polycyclic heteroaromatic compound of claim 7, wherein $X^1$, $X^2$, $X^3$, $X^4$, $X^5$, and $X^6$ are sulfur (S).

9. The fused polycyclic heteroaromatic compound of claim 1, wherein the compound has an average molecular weight of about 350 to about 3000.

10. An organic thin film comprising the fused polycyclic heteroaromatic compound according to claim 1.

11. An electronic device comprising the fused polycyclic heteroaromatic compound according to claim 1.

12. The electronic device of claim 11, wherein the electronic device is a transistor, an organic light emitting diode (OLED), a photovoltaic device, a solar cell, a laser device, a memory, or a sensor.

* * * * *